United States Patent
Natsuhara et al.

(10) Patent No.: US 8,981,091 B2
(45) Date of Patent: Mar. 17, 2015

(54) PEST CONTROL COMPOSITION

(75) Inventors: Katsuya Natsuhara, Tokyo (JP); Azusa Tanaka, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/233,561

(22) PCT Filed: Jul. 20, 2012

(86) PCT No.: PCT/JP2012/069071
§ 371 (c)(1),
(2), (4) Date: Jan. 17, 2014

(87) PCT Pub. No.: WO2013/012099
PCT Pub. Date: Jan. 24, 2013

(65) Prior Publication Data
US 2014/0187778 A1    Jul. 3, 2014

(30) Foreign Application Priority Data
Jul. 21, 2011  (JP) ................................. 2011-159711

(51) Int. Cl.
*A01N 43/76* (2006.01)
*A01N 43/54* (2006.01)

(52) U.S. Cl.
CPC ................ *A01N 43/76* (2013.01); *A01N 43/54* (2013.01)
USPC ......................................................... 544/319

(58) Field of Classification Search
USPC ......................................................... 544/319
See application file for complete search history.

(56) References Cited

U.S. PATENT DOCUMENTS

| | | |
|---|---|---|
| 5,478,855 A | 12/1995 | Suzuki et al. |
| 5,578,625 A | 11/1996 | Suzuki et al. |
| 2010/0216738 A1 | 8/2010 | Fischer et al. |

FOREIGN PATENT DOCUMENTS

| | | |
|---|---|---|
| CN | 102228055 A | 11/2011 |
| EP | 0326329 A2 | 8/1989 |
| WO | WO 93/22297 A1 | 11/1993 |

OTHER PUBLICATIONS

The International Preliminary Report on Patentability (PCT/IB/373), dated Jan. 21, 2014, issued in the corresponding International Application No. PCT/JP2012/069071.

*Primary Examiner* — Kristin Vajda
(74) *Attorney, Agent, or Firm* — Birch, Stewart, Kolasch & Birch, LLP

(57) ABSTRACT

Disclosed is a pest control composition having an excellent controlling effect on pests, which comprises etoxazole and fenazaquin.

6 Claims, No Drawings

PEST CONTROL COMPOSITION

TECHNICAL FIELD

The present application is filed claiming the priority of the Japanese Patent Application No. 2011-159711, the entire contents of which are herein incorporated by reference.

The present invention relates to a pest control composition and a pest control method.

BACKGROUND ART

Etoxazole, 2-(2,6-difluorophenyl)-4-[4-(1,1-dimethylethyl)-2-ethoxyphenyl]-4,5-dihydrooxazole) is known as an active ingredient of a pest control agent (see, e.g., Patent Literature 1).

Also, fenazaquin, 4-tert-butylphenethylquinazolin-4-yl ether, is known as an active ingredient of a pest control agent (see, e.g., Patent Literature 2).

CITATION LIST

Patent Literature

Patent Literature 1: WO93/22297
Patent Literature 2: EP0326329A

SUMMARY OF INVENTION

Technical Problem

An object of the present invention is to provide a pest control composition having an excellent control effect on pests and a pest control method.

Solution to Problem

The present inventors have intensively studied and finally found that a combination of etoxazole and fenazaquin has an excellent control effect on pests. Thus, the present invention has been completed.

Namely, the present invention includes the followings:
[1] A pest control composition comprising etoxazole and fenazaquin.
[2] The pest control composition according to the above [1], wherein the weight ratio of etoxazole to fenazaquin is from 5000:1 to 1:5000.
[3] The pest control composition according to the above [1], wherein the weight ratio of etoxazole to fenazaquin is from 300:1 to 1:4100.
[4] A pest control method, which comprises applying effective amounts of etoxazole and fenazaquin to a pest or an area where a pest lives.
[5] The pest control method according to the above [4], wherein the weight ratio of etoxazole to fenazaquin is from 5000:1 to 1:5000.
[6] The pest control method according to the above [4], wherein the weight ratio of etoxazole to fenazaquin is from 300:1 to 1:4100.
[7] Use of etoxazole and fenazaquin as a pest control agent.

Effects of Invention

The pest control composition of the present invention has an excellent control effect on pests.

DESCRIPTION OF EMBODIMENTS

The pest control composition of the present invention contains etoxazole and fenazaquin.

Etoxazole is a known compound and can be produced by a process described in, for example, WO93/22297.

Fenazaquin is described in, for example, EP0326329A and can be produced by a process described therein.

In the pest control composition of the present invention, the weight ratio of etoxazole to fenazaquin is, for example, from 5000:1 to 1:5000, from 500:1 to 1:5000, from 300:1 to 1:4100, from 250:1 to 1:4097, from 100:1 to 1:100, from 16:1 to 1:16 and from 1:3 to 1:16.

The pest control composition of the present invention may be a simple mixture of etoxazole and fenazaquin. However, the pest control composition of the present invention is generally prepared by mixing etoxazole and fenazaquin and an inert carrier, and if necessary a surfactant and the other formulation additives, and then formulating the mixture into a formulation such as oil solution, emulsifiable concentrate, suspension concentrate, wettable powder, water dispersible granules, dusts, or granules.

The pest control composition of the present invention contains etoxazole and fenazaquin in a total amount of generally 0.01 to 90% by weight, preferably 0.1 to 80% by weight.

Examples of the inert carrier include solid carriers, liquid carriers and gaseous carriers.

Examples of the solid carrier include fine powders and granules of minerals (e.g. kaolin clay, attapulgite clay, bentonite, montmorillonite, acidic white clay, pyrophylite, talc, diatomaceous earth, and calicite), natural organic substances (e.g. corncob flour, and walnut shell flour), synthetic organic substances (e.g. urea, and urea formaldehyde resin), salts (e.g. calcium carbonate, and ammonium sulfate), and synthetic inorganic substances (e.g. synthetic hydrated silicon oxide).

Examples of the liquid carrier include aromatic hydrocarbons (e.g. xylene, alkylbenzene, and methyl naphthalene), alcohols (e.g. 2-propanol), ketones (e.g. acetone, cyclohexanone, and isophorone), vegetable oils (e.g. soybean oil, and cotton oil), petroleum-based aliphatic hydrocarbons, esters, dimethylsulfoxide, acetonitrile, and water.

Examples of the gaseous carrier include fluorocarbon, butane gas, liquefied petroleum gas (LPG), dimethyl ether, and carbon dioxide.

Examples of the surfactant include anionic surfactants (e.g. alkyl sulfate ester salts, alkylaryl sulfonates, dialkyl sulfosuccinates, polyoxyethylene alkylaryl ether phosphate ester salts, ligninsulfonates, naphthalene sulfonate formaldehyde polycondensates, styrene-acrylate copolymers, and methyl oleyl taurate sodium salts), nonionic surfactants (e.g. polyoxyethylene alkylaryl ethers, polyoxyethylene alkylpolyoxypropylene block copolymers, and sorbitan fatty acid esters), and cationic surfactants (e.g. alkyl trimethyl ammonium salts).

Examples of the other formulation additives include water-soluble polymers (e.g., polyvinyl alcohol, and polyvinyl pyrrolidone), polysaccharides [e.g., gum arabic, alginic acid and a salt thereof, CMC (carboxymethyl cellulose), and xanthane gum], inorganic substances (e.g. aluminum magnesium silicate, smectite, and alumina-sol), preservatives (e.g. 5-chloro-2-methyl-4-isothiazolin-3-one, 1,2-benzothiazolin-3-one, and 2-bromo-2-nitropropane-1,3-diol), colorants, and stabilizers [e.g. PAP (isopropyl acid phosphate), and BHT (2,6-di-tert-butyl-4-methylphenol)].

Examples of the pest on which the pest control composition of the present invention has a controlling effect include arthropods such as insects and mites, and Nemathelminthes such as nematodes, as listed below.

Hemiptera:

Delphacidae such as *Laodelphax striatellus, Nilaparvata lugens*, and *Sogatella furcifera*; Deltocephalidae such as *Nephotettix cincticeps*, and *Nephotettix virescens*; Aphididae such as *Aphis gossypii, Myzus persicae, Brevicoryne brassicae, Macrosiphum euphorbiae, Aulacorthum solani, Rhopalosiphum padi*, and *Toxoptera citricidus*; Pentatomidae such as *Nezara antennata, Riptortus clavetus, Leptocorisa chinensis, Eysarcoris parvus, Halyomorpha mista*, and *Lygus lineolaris*; Aleyrodidae such as *Trialeurodes vaporariorum, Bemisia tabaci, Bemisia argentifolii*, and *Aleurocanthus spiniferus*; Coccidae such as *Aonidiella aurantii, Comstockaspis perniciosa, Unaspis citri, Ceroplastes rubens, Icerya purchasi*, and *Pseudaulacaspis pentagona*; Tingidae; Psyllidae; etc.

Lepidoptera:

Pyralidae such as *Chilo suppressalis, Tryporyza incertulas, Cnaphalocrocis medinalis, Notarcha derogata, Plodia interpunctella, Ostrinia furnacalis, Ostrinia nubilalis, Hellula undalis*, and *Pediasia teterrellus*; Noctuidae such as *Spodoptera litura, Spodoptera exigua, Pseudaletia separata, Mamestra brassicae, Agrotis ipsilon, Plusia nigrisigna, Thoricoplusia* spp., *Heliothis* spp., and *Helicoverpa* spp.; Pieridae such as *Pieris rapae*; Tortricidae such as *Adoxophyes* spp., *Grapholita molesta, Leguminivora glycinivorella, Matsumuraeses azukivora, Adoxophyes orana fasciata, Adoxophyes* sp., *Homona magnanima, Archips fuscocupreanus*, and *Cydia pomonella*; Gracillariidae such as *Caloptilia theivora*, and *Phyllonorycter ringoneella*; Carposinidae such as *Carposina niponensis*; Lyonetiidae such as *Lyonetia* spp.; Lymantriidae such as *Lymantria* spp., and *Euproctis* spp.; Yponomeutidae such as *Plutella xylostella*; Gelechiidae such as *Pectinophora gossypiella*, and *Phthorimaea operculella*; Arctiidae such as *Hyphantria cunea*; Tineidae such as *Tinea translucens*, and *Tineola bisselliella*; etc.

Thysanoptera:

Thripidae such as *Frankliniella occidentalis, Thrips palmi, Scirtothrips dorsalis, Thrips tabaci, Frankliniella intonsa*, and *Frankliniella fusca*; etc.

Diptera:

*Musca domestica, Culex pipiens pallens, Tabanus trigonus, Hylemya antiqua, Hylemya platura, Anopheles sinensis, Agromyza oryzae, Hydrellia griseola, Chlorops oryzae*; Agromyzidae such as *Liriomyza trifolii*; *Dacus cucurbitae, Ceratitis capitata*; etc.

Coleoptera:

*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda*, etc.

Orthoptera:

*Locusta migratoria, Gryllotalpa africana, Oxya yezoensis, Oxya japonica*, etc.

Hymenoptera:

*Athalia rosae, Acromyrmex* spp., *Solenopsis* spp., etc.

Blattodea:

*Blattella germanica, Periplaneta fuliginosa, Periplaneta americana, Periplaneta brunnea, Blatta orientalis*, etc.

Acarina:

Tetranychidae such as *Tetranychus urticae, Panonychus citri*, and *Oligonychus* spp.; Eriophyidae such as *Aculops pelekassi*; Tarsonemidae such as *Polyphagotarsonemus latus*; Tenuipalpidae; Tuckerellidae; Acaridae such as *Tyrophagus putrescentiae*; Pyroglyphidae such as *Dermatophagoides farinae*, and *Dermatophagoides ptrenyssnus*; Cheyletidae such as *Cheyletus eruditus, Cheyletus malaccensis*, and *Chelacaropsis moorei*; etc.

Nematoda:

*Aphelenchoides besseyi, Nothotylenchus acris*, etc.

The pest control method of the present invention comprises applying effective amounts of etoxazole and fenazaquin to a pest or an area where a pest lives.

Herein, the "effective amounts" mean the total amount of etoxazole and fenazaquin in which amount the application of both compounds can make a pest controlled.

Examples of the area where a pest lives include crops and soil where crops are grown.

The pest control method of the present invention can be carried out by applying the pest control composition of the present invention to a pest or an area where a pest lives. The pest control method of the present invention can be also carried out by applying etoxazole and fenazaquin separately to a pest or an area where a pest lives.

In the pest control method of the present invention, the weight ratio of etoxazole to fenazaquin is, for example, from 5000:1 to 1:5000, from 500:1 to 1:5000, from 300:1 to 1:4100, from 250:1 to 1:4097, from 100:1 to 1:100, from 16:1 to 1:16 and from 1:3 to 1:16.

In the pest control method of the present invention, application of etoxazole and fenazaquin can be carried out by, for example, spraying the foliage of crops with etoxazole and fenazaquin, irrigating soil where crops are grown with etoxazole and fenazaquin, or treating the seeds of crops with etoxazole and fenazaquin.

When etoxazole and fenazaquin are applied to the foliage of crops or the soil where crops are grown, the application rate is generally from 0.1 to 1000 g per 10000 $m^2$, preferably from 1 to 200 g per 10000 $m^2$, in terms of the total amount of etoxazole and fenazaquin, although it may be varied depending on the kinds of crops to be protected from pests, the kinds of target pests, the population size of target pests, the type of a formulation, the application period, and climate conditions.

When the seeds of crops are treated with etoxazole and fenazaquin, the treatment rate is generally from 0.001 to 20 g, preferably from 0.01 to 10 g per 1 kg of seeds, in terms of the total amount of etoxazole and fenazaquin.

When etoxazole and fenazaquin are formulated into emulsifiable concentrate, wettable powder or suspension concentrate, the formulation is generally diluted with water and then sprayed. In this case, the formulation is diluted so that the total concentration of etoxazole and fenazaquin becomes generally from 1 to 10000 ppm, preferably from 10 to 500 ppm.

When etoxazole and fenazaquin are formulated into dusts or granules, the formulation is generally applied as it is without diluting it.

The pest control composition of the present invention can be used in pest control for plants including, but not limited to, "crops" listed below.

"Crops":

Agricultural crops: corn, wheat, barley, rye, oat, sorghum, cotton, soybean, kidney bean, azuki bean, rice, peanut, sarrazin, sugar beet, rapeseed, sunflower, sugar cane, tobacco etc.;

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, chard, etc.), Labiatae vegetables (Japanese basil, mint, basil, etc.), strawberry, sweat potato, yam, aroid etc.;

Flowers and ornamental plants: *acanthus*, morning glory, azalea, *hydrangea, anemone raddeana, rhodohypoxis baurii; anemone, polygonatum odoratum, amaryllis, iris, alyssum, armeria, arctotis*, China aster, edible flower, *Bauera ruibioides*, Cuban lily, *Hosta montana*, Mexican aster, four o'clock, *Hypericum*, oriental poppy, *gentiana makinoi, Hosta aureomarginata*, Japanese iris, *clematis patens, gazania*, Casa Blanca, carnation, showy lily, *gerbera, kalanchoe, calceolaria*, curry plant, Carolina jasmine, canna, *chrysanthemum, Brugmansia*, yellow cosmos, plantain lily, KimJongilia, tea tree (Manuka), pot marigold, myrtle, *nasturtium, gladiolus*, Siam tulip, *clematis*, cockscomb, shrimp plant, midday flower, cosmos, *Hosta sieboldii, Convolvulus arvensis, Hosta sagae*, primrose, saffron crocus, *salvia, cyclamen*, moss phlox, *Paeonia lactiflora, Anemone hupehensis, Bletilla striata*, sweet pea, lily of the valley, snowflake, *portulaca*, violet, rose of Sharon, yarrow, Chinese pink, *zephyranthes, pelargonium, geum*, zepher lily, *dahlia, tithonia*, tulip, chocolate cosmos, *Vinca major, scilla*, downy myrtle, German iris, passionflower, *dianthus*, rape blossom, Madagascar periwinkle, soft windflower, *nemophila, Nerine*, swamp chrysanthemum (North pole), Japanese water iris (*iris ensata* var. *spontanea*), *verbena, hibiscus*, Joseph's coat, coral flower, Japanese water iris (*Iris ensata*), eastern redbud, spring starflower, wavyleaf sea-lavender, California poppy, pansy, Virginia stock, daisy, corn poppy, Himalayan creeping saxifrage, sunflower, hyacinth, crape-myrtle, *Geranium, fuchsia, freesia, primula*, garden balsam, ground-cherry, peony, *Tricyrtis*, marguerite, marigold, *Gymnaster savatieri*, strawflower, *muscari*, Japanese kerria, lily, *ranunculus, lantana, gentian, Lupinus, lobelia*, etc.;

Ornamental foliage plants: ivy, cat tail, *aglaonema, adiantum, asparagus, asplenium, ananas, aphelandra, alocasia, anthurium*, Indian rubber tree, *nepenthes, aechmea, aeschynanthus, episcia, strelitzia augusta*, spiders plant, Chinese banyan, kapok, *caladium, calathea*, velvet plant (*Gynura*), *Guzumania, Ctenanthe*, gum tree, *crassula, croton, Alocasia odora*, orange jessamine, coffee tree, *massangeana*, conifers, *coleus, cordyline, columnea, sansevieria, sansevieria*, Chinese ixora, *schefflera, cissus, cyperus*, reed rhapis, silk jessamine, *syngonium, strelitzia, spathiphyllum, senecio, zebrina*, Japanese sago palm, *tillandsia, tupidanthus*, coral tree, *dizygotheca, dieffenbachia, duranta*, bottle palm, *dracaena, tradescantia, neoregelia, nephrolepis*, hearts vine, *hibiscus, pachypodium*, Guiana chestnut (*Pachira*), ponytail, staghorn fern, *pilea, fatshedera, ficus pumila, philodendron, bougainvillea, phoenix, fittonia, pteris*, bridal veil, *vriesea, plectranthus, begonia, peperomia, heliconia, benjamina*, poinsettia, *pothos, hoya, maranta*, Belgian evergreen, milkbush, oyster plant, *monstera*, palm, *yucca, lantana*, etc.;

Fruit trees: pomaceous fruits (apple, common pear, Japanese pear, Chinese quince, quince, etc.), stone fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, etc.;

Trees other than fruit trees: tea, mulberry, flowering trees and shrubs, street trees (ash tree, birch, dogwood, *eucalyptus, ginkgo*, lilac, maple tree, oak, poplar, *cercis*, Chinese sweet gum, plane tree, *zelkova*, Japanese arborvitae, fir tree, Japanese hemlock, needle juniper, pine, spruce, yew), etc.

The above-described "crops" include plants having the resistance to herbicides which is imparted by a classic breeding method or a genetic engineering technique.

In the present invention, etoxazole and fenazaquin may be used in admixture with or in combination with other active ingredients such as other insecticides, acaricides, nematocides, fungicides, herbicides, plant hormones, and plant growth regulators; synergists; safeners; pigments, fertilizers; soil conditioners; and/or animal feed.

EXAMPLES

Hereinafter, the present invention is described specifically by way of Formulation Examples and Test Examples to which the present invention is not limited.

First, Formulation, Examples are described. In Examples, the term "part(s)" means part(s) by weight.

Formulation Example 1

Five parts of etoxazole, 5 parts of fenazaquin, 8 parts of polyoxyethylene styrylphenyl ether, 2 parts of calcium dodecylbenzenesulfonate, and 80 parts of xylene are mixed to obtain an emulsifiable concentrate.

Formulation Example 2

A mixture of 20 parts of etoxazole, 4 parts of fenazaquin, 3 parts of sodium dodecylbenzenesulfonate, 3 parts of sodium ligninsulfonate, and 70 parts of diatomaceous earth is pulverized in a jet air mill to obtain a wettable powder.

Formulation Example 3

One part of etoxazole, 0.5 parts of fenazaquin, 48.5 parts of talc, and 50 parts of clay are mixed to obtain dusts.

Formulation Example 4

A mixture of 1 part of etoxazole, 4 parts of fenazaquin, 5 parts of sodium dodecylbenzenesulfonate, 30 parts of bentonite, and 60 parts of clay is stirred with an appropriate amount of water, granulated in a granulator, and then dried under ventilation to obtain granules.

Formulation Example 5

To a mixture of 5 parts of polyoxyethylene styrylphenyl ether sulfate, 20 parts of a 1% aqueous xanthan gum solution, 3 parts of a smectite mineral, and 60 parts of water are added 5 parts of etoxazole and 5 parts of fenazaquin. The mixture is stirred and then wet ground in a sand mill to obtain a suspension concentrate.

Formulation Example 6

Firstly, 0.1 part of etoxazole and 0.02 parts of fenazaquin are solved in 10 parts of acetone. Then, the solution is uniformly mixed with 99.88 parts of animal solid feed powder (CE-2: a solid powdery diet for growing and breeding manufactured by CLEA Japan, Inc.), and then the acetone is removed by air drying to obtain a poison bait.

Formulation Example 7

Firstly, 0.1 part of etoxazole and 0.1 part of fenazaquin are solved in 5 parts of xylene and 5 parts of trichloroethane.

Then, the solution is mixed with 89.8 parts of deodorized kerosene to obtain an oil solution.

Next, Test Examples for pest control by the present invention are described.

Test Example 1

Kidney beans (Nagauzura saitou) were planted (one plant per container) in plastic containers (volume: 90 ml) and grown until the primary leaves had fully expanded. Only one leaf of each kidney bean plant was left on the plant and all the other leaves were removed from the plant. Then, 5 adults of *Tetranychus urticae* were released on each leaf.

A suspension concentrate containing 10.0% by weight of etoxazole [product name: Baroque (registered trademark) flowable, manufactured by Kyoyu Agri Co., Ltd.] was diluted with water containing 0.02% by volume of a spreading agent [product name: Sindain (registered trademark), manufactured by Sumitomo Chemical Co., Ltd.] so that the concentration of etoxazole became 12.5 ppm.

A reference standard containing 99.9% by weight of fenazaquin was diluted with water containing 0.02% by volume of a spreading agent [product name: Sindain (registered trademark), manufactured by Sumitomo Chemical Co., Ltd.] so that the concentration of fenazaquin became 50 ppm.

The water dilution of etoxazole, the water dilution of fenazaquin, and water containing 0.02% by volume of a spreading agent [product name: Sindain (registered trademark), manufactured by Sumitomo Chemical Co., Ltd.] were mixed to prepare a test solution with a predetermined concentration of etoxazole and fenazaquin.

Three days after the release of the insects, each test solution was sprayed onto the leaves of kidney bean plants and the leaves were air-dried. Two days after the treatment, the tested insects were observed for life or death. An insect death rate was calculated according to the following equation. For each treatment there are duplicates. Results are shown in Table 1.

Insect death rate (%)=100×(number of dead insects/number of tested insects)

TABLE 1

| Etoxazole Concentration (ppm) | Fenazaquin Concentration (ppm) | Insect death rate (%) |
|---|---|---|
| 0.000781 | — | 10 |
| — | 3.2 | 40 |
| 0.000781 | 3.2 | 90 |

Test Example 2

Kidney beans (Nagauzura saitou) were planted (one plant per container) in plastic containers (volume: 90 ml) and grown until the primary leaves had fully expanded. Only one leaf of each kidney bean plant was left on the plant and all the other leaves were removed from the plant. Then, 10 adults of *Tetranychus urticae* were released on each leaf.

A suspension concentrate containing 10.0% by weight of etoxazole [product name: Baroque (registered trademark) flowable, manufactured by Kyoyu Agri Co., Ltd.] was diluted with water containing 0.02% by volume of a spreading agent [product name: Sindain (registered trademark), manufactured by Sumitomo Chemical Co., Ltd.] so that the concentration of etoxazole became 50 ppm.

A reference standard containing 99.9% by weight of fenazaquin was diluted with water containing 0.02% by volume of a spreading agent [product name: Sindain (registered trademark), manufactured by Sumitomo Chemical Co., Ltd.] so that the concentration of fenazaquin became 50 ppm.

The water dilution of etoxazole, the water dilution of fenazaquin, and water containing 0.02% by volume of a spreading agent [product name: Sindain (registered trademark), manufactured by Sumitomo Chemical Co., Ltd.] were mixed to prepare a test solution with a predetermined concentration of etoxazole and fenazaquin.

Four days after the release of the insects, each test solution was sprayed onto the leaves of kidney bean plants and the leaves were air-dried. Three days after the treatment, the tested insects were observed for life or death. An insect death rate was calculated according to the following equation. For each treatment there are duplicates. Results are shown in Table 2.

Insect death rate (%)=100×(number of dead insects/number of tested insects)

TABLE 2

| Etoxazole Concentration (ppm) | Fenazaquin Concentration (ppm) | Insect death rate (%) |
|---|---|---|
| 0.8 | — | 15 |
| — | 3.2 | 40 |
| — | 12.5 | 50 |
| 0.8 | 3.2 | 60 |
| 0.8 | 12.5 | 95 |

Test Example 3

Cabbages (Green ball) were planted (one plant per container) in plastic containers (volume: 90 ml) and grown until the third to fourth leaf stage. Only one leaf of each cabbage plant was left on the plant and all the other leaves were removed from the plant. The plastic containers were put into a net cage containing a lot of living *Bemisia tabaci* and allowed to stand for 24 hours. After that, the plastic containers were taken out from the cage and the number of living insects (*Bemisia tabaci*) on the cabbage seedlings was determined (This is called the "number of insects before treatment").

A suspension concentrate containing 10.0% by weight of etoxazole [product name: Baroque (registered trademark) flowable, manufactured by Kyoyu Agri Co., Ltd.] was diluted with water containing 0.02% by volume of a spreading agent [product name: Sindain (registered trademark), manufactured by Sumitomo Chemical Co., Ltd.] so that the concentration of etoxazole became 800 ppm.

A reference standard containing 99.9% by weight of fenazaquin was diluted with water containing 0.02% by volume of a spreading agent [product name: Sindain (registered trademark), manufactured by Sumitomo Chemical Co., Ltd.] so that the concentration of fenazaquin became 50 ppm.

The water dilution of etoxazole, the water dilution of fenazaquin, and water containing 0.02% by volume of a spreading agent [product name: Sindain (registered trademark), manufactured by Sumitomo Chemical Co., Ltd.] were mixed to prepare a test solution with a predetermined concentration of etoxazole and/or fenazaquin.

Then, each test solution was sprayed onto the plastic containers to sufficiently soak cabbage seedlings, and allowed to stand for room temperature (about 25° C.). Two days after the treatment, the number of living insects (*Bemisia tabaci*) on the cabbage seedlings was determined (This is called the "number of insects after treatment").

An insect death rate was calculated according to the following equation. For each treatment there are duplicates. Results are shown in Table 3.

$$\text{Insect death rate (\%)} = 100 - (\text{number of insects after treatment}/\text{number of insects before treatment}) \times 100$$

TABLE 3

| Etoxazole Concentration (ppm) | Fenazaquin Concentration (ppm) | Insect death rate (%) |
|---|---|---|
| 50 | — | 15 |
| 200 | — | 17 |
| 800 | — | 32 |
| — | 3.2 | 11 |
| — | 50 | 64 |
| 50 | 3.2 | 65 |
| 200 | 3.2 | 82 |
| 800 | 3.2 | 63 |
| 50 | 50 | 100 |
| 200 | 50 | 100 |
| 800 | 50 | 100 |

The invention claimed is:

1. A pest control composition comprising etoxazole and fenazaquin.

2. The pest control composition according to claim 1, wherein the weight ratio of etoxazole to fenazaquin is from 5000:1 to 1:5000.

3. The pest control composition according to claim 1, wherein the weight ratio of etoxazole to fenazaquin is from 300:1 to 1:4100.

4. A pest control method, which comprises applying effective amounts of etoxazole and fenazaquin to a pest or an area where a pest lives.

5. The pest control method according to claim 4, wherein the weight ratio of etoxazole to fenazaquin is from 5000:1 to 1:5000.

6. The pest control method according to claim 4, wherein the weight ratio of etoxazole to fenazaquin is from 300:1 to 1:4100.

* * * * *